United States Patent
De Bandt et al.

(10) Patent No.: US 9,533,946 B1
(45) Date of Patent: Jan. 3, 2017

(54) N-CARBAMOYLPUTRESCINE TO ENHANCE MUSCLE PROTEIN SYNTHESIS

(71) Applicant: CITRAGE, Créteil (FR)

(72) Inventors: Jean-Pascal De Bandt, Croissy sur Seine (FR); Luc Cynober, Sceaux (FR); David Ramani, Boulogne-Billancourt (FR); Christiane Garbay, Paris (FR)

(73) Assignee: CITRAGE, Créteil (FR)

( * ) Notice: Subject to any disclaimer, the term of this patent is extended or adjusted under 35 U.S.C. 154(b) by 0 days.

(21) Appl. No.: 15/164,590

(22) Filed: May 25, 2016

(51) Int. Cl.
| | | |
|---|---|---|
| *C07C 275/14* | (2006.01) | |
| *A61K 8/42* | (2006.01) | |
| *A61Q 19/00* | (2006.01) | |
| *A23L 1/30* | (2006.01) | |
| *A23L 1/305* | (2006.01) | |

(52) U.S. Cl.
CPC ............... *C07C 275/14* (2013.01); *A23L 1/30* (2013.01); *A23L 1/3051* (2013.01); *A61K 8/42* (2013.01); *A61Q 19/00* (2013.01); *A23V 2002/00* (2013.01)

(58) Field of Classification Search
None
See application file for complete search history.

(56) References Cited

FOREIGN PATENT DOCUMENTS

| EP | 2583566 A1 | 4/2013 |
|---|---|---|
| EP | 2875736 A1 | 5/2015 |

OTHER PUBLICATIONS

Database CAPLUS Chemical Abstracts Service, Columbus, Ohio, US; Database Accession No. 1995:553479, Abstract of Mendum et al., Univ. of California, Davis, CA, USA (1994) 151 pp. Univ. Microfilms Int., Order No. DA9504556 From: Diss. Abstr. Int. B 1995, 55(10), 4199.*
Database CAPLUS Chemical Abstracts Service, Columbus, Ohio, US; Database Accession No. 1984:34297, Abstract of Srivenugopal et al., Methods in Enzymology (1983), 94(Polyamines), 429-30.*
Nicole K. L. Lee et al., "Polyamines, Androgens, and Skeletal Muscle Hypertrophy," Journal of Cellular Physiology, vol. 226, No. 6, Jun. 2011, pp. 1453-1460.
Yuval Ramot et al., "Spermidine Promotes Human Hair Growth and Is a Novel Modulator of Human Epithelial Stem Cell Functions," PLOS ONE, vol. 6., No. 7, Jul. 2011, pp. 1-12.
D. Ramani et al., "N-Carbamoylputrescine, a citrulline-derived polyamine, is not a significant citrulline metabolite in rats," Analytical Biochemistry, vol. 423, 2012, pp. 54-60.
Joanna Godzien et al., "Effect of a nutraceutical treatment on diabetic rats with targeted CE-MS non-targeted approaches," Mar. 2013, vol. 9, pp. 188-202.
European Search Report issued in European Patent Application No. 13306618 dated Feb. 24, 2014.

* cited by examiner

*Primary Examiner* — Karl J Puttlitz
(74) *Attorney, Agent, or Firm* — Arent Fox LLP

(57) ABSTRACT

The present invention relates to the field of food supplement and medicament supporting muscle metabolism, more precisely muscle protein synthesis. In particular, the invention relates to a composition comprising N-carbamoylputrescine (NCP). The invention further relates to the non-therapeutic use of N-carbamoylputrescine (NCP) to enhance muscle protein synthesis in a subject. Moreover, the invention also relates to N-carbamoylputrescine for its use as a medicament.

8 Claims, 1 Drawing Sheet

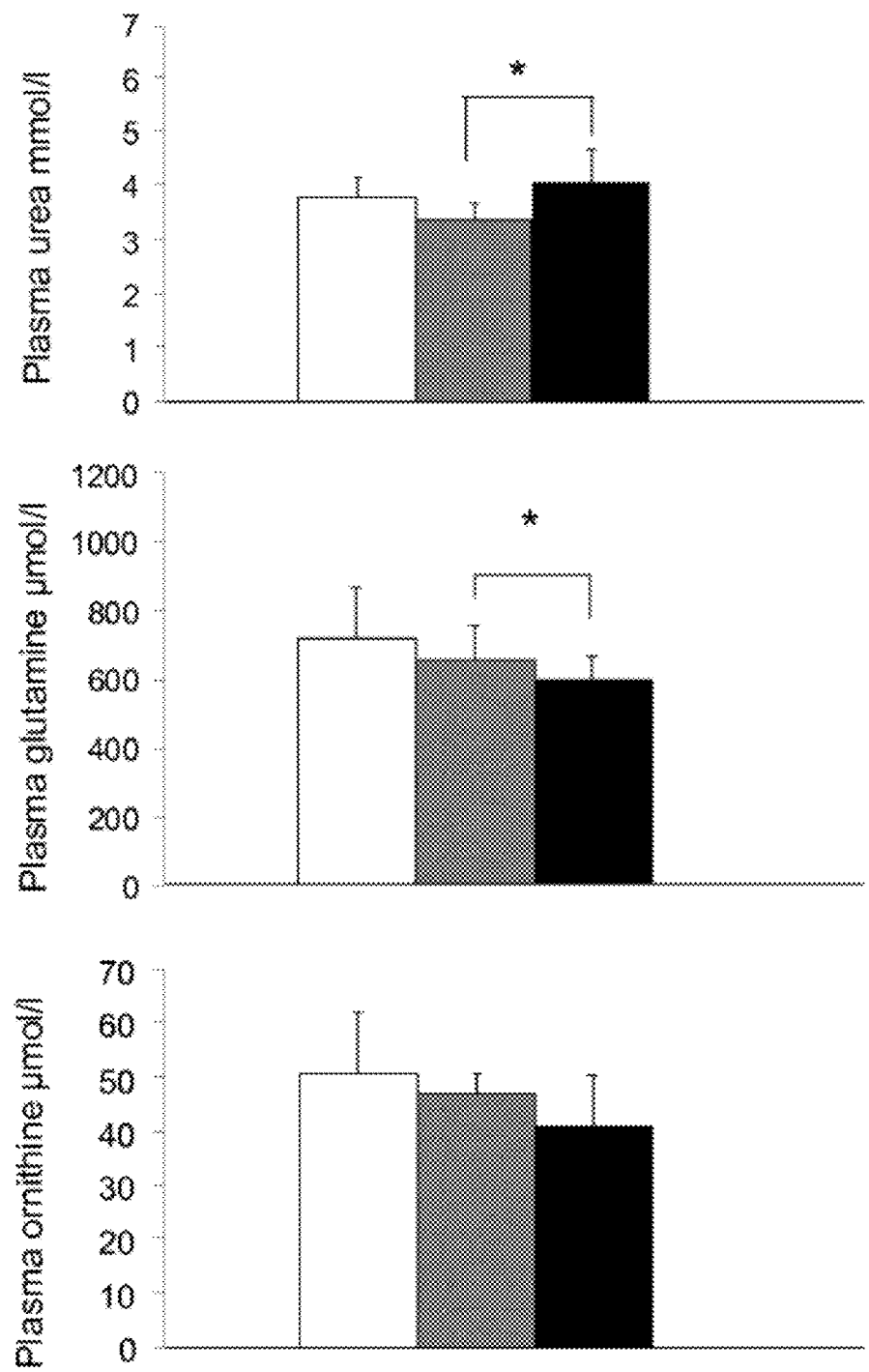

N-CARBAMOYLPUTRESCINE TO ENHANCE MUSCLE PROTEIN SYNTHESIS

FIELD OF THE INVENTION

The present invention relates to the field of food supplement and medicament supporting muscle metabolism, more precisely muscle protein synthesis. In particular, the invention relates to a composition comprising N-carbamoylputrescine (NCP). The invention further relates to the non-therapeutic use of N-carbamoylputrescine (NCP) to enhance muscle protein synthesis in a subject. Moreover, the invention also relates to N-carbamoylputrescine for its use as a medicament.

BACKGROUND

Muscle metabolism is affected by many different processes such as physical activity and age. For example, muscle protein synthesis is increased by elevated level of physical exercise, such as in the case of athletes. Muscle protein synthesis is also known to be more important in children during growth than in adults. Indeed, during growth and until they are adults, children gain a large mass of muscle, predominantly of skeletal muscle rich in type I fibers, also called slow twitch fiber rich muscles. Muscle enrichment in type I fibers is favored by endurance exercise and thwarted by physical inactivity. Muscle enrichment in type I fibers is considered a favorable factor in the prevention of metabolic syndrome and related disorders.

Different products have been found that promote protein synthesis. However, skeletal muscle fibers are not all the same. Indeed, in comparison with fast twitch muscles, slow twitch muscles tend to have a low activity level of ATPase, a slower speed of contraction with a less developed glycolytic capacity. They have been demonstrated to have high concentrations of mitochondrial enzymes, thus they are fatigue resistant. Importantly, research has shown that protein synthesis is differently regulated depending on the muscle fiber type (Goodman et al., PLoS One; 7(5); 2012). Despite this very well-known fact, no product has been discovered yet that can increase muscle protein synthesis specifically in slow twitch fiber-rich muscles. Moreover, most of the existing products have proven adverse effects, and would probably not be safe for a child.

EP 2 583 566 for example discloses whey protein micelles, susceptible to enhance muscle mass and performance. However, while whey protein micelles represent an optimized form of protein supply, they do not promote protein synthesis on the long term and do not specifically improve protein synthesis of type I muscle fibers, nor muscle mass and performance in slow twitch fiber rich muscles. In addition, high doses of whey protein can cause some side effects such as increased bowel movements, nausea, thirst and may in the long term compromise kidney function.

WO 2001/056402 discloses alpha lipoic acid-based food supplement able to increase lean muscle mass and strength, yet this increase does not seem to occur specifically in slow twitch fiber-rich muscles. Moreover, alpha lipoic acid may induce skin rash in humans. Further, it is recommended that people with diabetes be particularly cautious when taking alpha lipoic acid, because it affects blood sugar regulation.

Some products intended for increasing muscle mass claim to have low to no side effects. For instance, FR 2 907 011 discloses that the use of citrulline increases protein synthesis in the muscle with no side effect. Yet, the administration of citrulline does not appear to enable an increase in protein synthesis specifically in type I muscle fibers.

Therefore, to date, no product has been shown to be able to support or enhance muscle protein synthesis specifically in slow twitch fiber-rich muscles, with low to no toxicity.

There is thus a need for improved compositions for enhancing muscle protein synthesis in a subject, which do not present adverse effects and target preferably skeletal muscles.

On the other hand, most muscle-wasting associated disorders, and in particular wasting which occurs with ageing, have currently no cure, and patients would obviously benefit from any medication capable of preventing or treating those disorders.

Hence, there is also a need for medicaments for the prevention or treatment of muscle-wasting associated disorders.

DETAILED DESCRIPTION OF VARIOUS EMBODIMENTS

The inventors have found that the administration of N-carbamoylputrescine (compound of formula (I) hereafter) to mammals can enhance protein synthesis in muscle. The inventors found that the administration of N-carbamoylputrescine increases protein synthesis in muscles, most particularly in slow twitch fiber-rich muscles. Interestingly, no side effects were noticed subsequently to N-carbamoylputrescine administration.

This result was unexpected and unpredictable in view of the present state of the art, since no such properties have been disclosed so far for other compounds. Moreover, while N-carbamoylputrescine is known to be present in plants and bacteria (Janowitz et al., FEBS Lett., 544(1-3):258-61, 2003), there is no evidence of its presence in mammalian tissues (Ramani et al., Anal Biochem, 423(1):54-60, 2012). It was therefore very unlikely that it would play a physiological role in muscle protein synthesis.

The inventors moreover found that N-carbamoylputrescine can advantageously be used either for non-therapeutic purpose in healthy subjects, or for therapeutic purposes, particularly in subjects suffering from a muscle wasting associated disorder, and for example for the protection against the loss of muscle mass and function.

A first object of the invention is thus a composition comprising N-carbamoylputrescine and/or one of its salts.

According to the invention, the terms "N-carbamoylputrescine" refer to N-substituted putrescine where the N substituent is a carbamoyl group. Preferably, the terms "N-carbamoylputrescine" refer to the molecule 1-(4-aminobutyl) urea of formula (I) (CAS Registry Number: 6851-51-0).

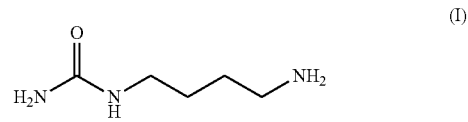

(I)

N-carbamoylputrescine can easily be prepared by methods well known from the skilled person. In particular, N-carbamoylputrescine can be chemically synthesized from putrescine (CAS Registry Number: 110-60-1) and potassium cyanate (CAS Registry Number: 590-28-3) by the method described in Ramani et al. (Anal Biochem, 423(1):54-60, 2012). N-carbamoylputrescine can also be produced from barley leaves according to the process described by Smith and Garraway (Phytochemistry 1964; 3; 23-6).

Alternatively, N-carbamoylputrescine can be produced in microorganisms expressing recombinant arginine decarboxylase and recombinant agmatine iminohydrolase but not the subsequent enzymes of this metabolism pathway (in particular N-carbamoylputrescine amidohydrolase and putrescine transcarbamylase). Synthesis by recombinant DNA techniques, are well known from the person skilled in the art, and are further thoroughly detailed in Sambrook et al. (CSHL Press, 2001) and Ausubel et al. (John Wiley & Sons, 1988).

According to the invention, the terms "salts of N-carbamoylputrescine" refer to salts of N carbamoylputrescine derived from inorganic and organic acids. Non-limitative examples of acids suitable for the invention include hydrochloric, sulfuric, fumaric, maleic, phosphoric, glycolic, lactic, succinic, tartaric, acetic, citric, methanesulfonic acids. The salts of the invention can easily be prepared by methods well-known from the art such as disclosed in WO 2012/040139 for instance.

The composition comprising N-carbamoylputrescine and/or at least one of its salts can be formulated according to any method known in the art, depending on its intended use.

In a particular embodiment, the composition of the invention is formulated for oral administration. For example, for a more pleasurable and convenient administration, the composition can advantageously be formulated as an edible product, such as food or beverage.

Preferably, the composition of the invention, formulated for oral administration, is an edible product. According to the invention, the terms "edible product" refer to products and compositions in any physical form which are intended to be consumed by human beings or lower animals in whole or part via the oral cavity.

Preferably, the edible product is chosen from the group consisting of food products and beverage products.

According to the invention, the terms "food product" refer to edible products in a fluid, semi-fluid or solid form. Preferably, the term food product encompasses all food-based compositions, as well as dietary supplements. According to the invention, the terms "beverage product" refer to edible products in a liquid form.

Most compounds that are taken orally are generally absorbed by the cells of the intestinal tract, which require that they overcome the acidic environment of the stomach. In order to increase intestinal absorption, the skilled person may use delivery vehicles suitable for gastrointestinal delivery. One particularly advantageous way to achieve that goal is to coat the compounds of interest with an outer enteric vehicle, also called enteric coating.

Thus, in a preferred embodiment, the edible product of the invention comprises at least N carbamoylputrescine or one of its salts, and an enteric vehicle.

By "enteric vehicle" it is herein referred to any vehicle that is not degraded by the fluids and enzymes in the stomach. According to the invention, suitable enteric vehicle include pH-triggered coatings, pressure-sensitive coatings or time-released coatings. Such coatings are well known from the skilled person, who can for instance further refer to U.S. Pat. No. 5,851,579, and G. Agyilirah and G. S. Banker (Polymers For Enteric Coating Applications, P. J. Tarcha ed., CRS Press, 1991). Preferably, an enteric vehicle is a vehicle that is not degraded at a pH of 5 or below. More preferably, an enteric vehicle is a vehicle that is not degraded at pH from 5 to 2.

Moreover, the edible product of the invention can be improved by the addition of further edible compounds of interest, which may either enhance or complete the effect of N-carbamoylputrescine.

Preferably, the edible product according to the invention further comprises at least one compound selected from the group consisting of L-amino-acids, polyamines or carbohydrate compounds.

By "L-amino-acid", it is herein referred to an organic levorotatory compound comprising amine ($-NH_2$) and carboxylic acid ($-COOH$) functional groups, along with a side-chain specific to each amino acid.

Preferably, the L-aminoacid according to the invention is selected from the group consisting of Histidine, Isoleucine, Leucine, Lysine, Methionine, Phenylalanine, Threonine, Tryptophan, Valine, Alanine, Arginine, Citrulline, Asparagine, Aspartic acid, Cysteine, Glutamic acid, Glutamine, Glycine, Ornithine, Proline, Serine, Tyrosine, Argininosuccinate, decarboxylated forms thereof and deaminated forms thereof.

By "polyamine", it is herein referred to an organic compound comprising two or more primary amino groups ($-NH_2$)

Preferably, the polyamine according to the invention is selected from the group consisting of putrescine, spermine, spermidine, and agmatine.

By "carbohydrate compound", it is herein referred to an organic compound that consists only of carbon, hydrogen, and oxygen atoms. Preferably, the carbohydrate compound has a hydrogen:oxygen atom ratio of 2:1.

Preferably, the carbohydrate compound according to the invention is selected from the group consisting of glucose, fructose, galactose, and polysaccharides thereof.

By "polysaccharides of glucose, fructose, galactose", it is herein referred to polysaccharides of glucose, polysaccharides of fructose, polysaccharides of galactose, polysaccharides of glucose and fructose, polysaccharides of glucose and galactose, and polysaccharides of galactose and fructose. Preferably, the polysaccharide of glucose, fructose, galactose of the invention is selected from the group consisting of saccharose, maltose or lactose. Most preferably, the polysaccharide of glucose, fructose, galactose of the invention is saccharose.

In another embodiment, the composition of the invention is formulated for topic administration, more particularly for dermatological administration. Topic administration can be obtained by formulating the composition of the invention into forms suitable for that use. For instance, the composition of the invention can be formulated into cosmetic compositions such as gels, creams or lotions.

Preferably, the composition of the invention, formulated for topic administration, is a topical cosmetic composition.

By "topical cosmetic composition", it is herein referred to a solid, liquid or semi-solid composition, particularly intended for topic administration. Topical cosmetic compositions according to the invention can be in solid, liquid or semi-solid forms. Topical cosmetic compositions in solid forms can comprise for example powders, aerosols and plasters. Topical cosmetic compositions in liquid forms comprise for example lotions, liniments, solutions, emulsions and suspensions. Cosmetic compositions in liquid forms can comprise for instance ointments, creams, paste and gels.

It is well known to the skilled person that absorption of an active compound by the skin may be enhanced by excipients, preferably chosen according to the contemplated way of administration.

As it is intended for topical application, the composition of the invention may further comprise a cosmetically acceptable carrier or excipient, especially a carrier or excipient suitable for topical administration, that is to say a carrier or excipient compatible with the skin.

By "cosmetically acceptable excipient" it is herein referred to excipients suitable with a cosmetical use, thus excipients compatible with the skin. The cosmetical excipient can for example be chosen among excipients conventionally used in cosmetics, in particular topical cosmetics, such as pigments, dyes, polymers, surfactants, rheological agents, fragrances, electrolytes, pH modifiers, preservatives and mixtures thereof.

Another object of the invention is the non-therapeutic use of N-carbamoylputrescine, or of one of its salts, or of an edible product or of a topical cosmetic composition according to the invention, to enhance muscle protein synthesis in a subject.

According to the invention, the terms "non-therapeutic use" refer to a use that does not allow and/or is not intended for the prevention nor for the treatment of a pathological state. By "prevention" is herein referred to the measures taken for reducing the risk of occurrence of the pathological state under consideration.

The inventors have found that the administration of N-carbamoylputrescine is particularly effective for enhancing protein synthesis in slow twitch fiber rich muscles.

According to the invention, the terms "enhance muscle protein synthesis" refer to the increase of protein synthesis in the overall muscle mass of the subject. Preferably, the terms "enhance muscle protein synthesis" refer to the increase of protein synthesis in slow twitch fiber rich muscles of the subject.

Thus, the invention also relates to the non-therapeutic use of N-carbamoylputrescine, or of one of its salts, or of an edible product or of a topical cosmetic composition according to the invention, to enhance protein synthesis in slow twitch fiber rich muscles in a subject.

By "slow twitch fiber rich muscles", it is herein referred to muscles rich in type I muscle fiber, that is to say muscles which fibers comprise more than 50% type I muscle fibers. By type I muscle fiber, it is herein referred to muscle fibers comprising the myosin heavy chain beta (MHC-B) isoform encoded by the MYH7 gene (NCBI gene reference: 4625).

Enhancement of said muscle protein synthesis can be assayed by the person skilled in the art with stable isotope-based methods, such as described in Dangin et al. (J Nutr.; 132:3228S-33S; 2002).

A non-therapeutic use according to the invention can for example be the enhancement of physiological aspects or physiological reactions in the subject. Preferably, the non-therapeutic use of the invention is to increase muscle mass, muscle strength and/or muscle performance.

According to the invention, the terms "increase muscle mass" refer to the increase of the overall muscle mass of the subject. The muscle mass can easily be evaluated by the person skilled in the art by computerized tomography (CT scan), such as described in Baracos et al. (Am J Clin Nutr. 2010; 91:1133S-1137S).

According to the invention, the terms "increase muscle strength" refer to the increase in the force generated by a contraction of said muscle. The force generated by a contraction can be measured non-invasively for instance using hand-grip strength determination, such as described in Granger et al. (BMC Cancer. 2013; 13:135).

According to the invention, the terms "increase muscle performance" refer to the increase in the efficiency of said muscle. In the context of the invention, the efficiency of a muscle is defined as the ratio of mechanical work output to the total metabolic cost. The efficiency of a muscle can be calculated from oxygen consumption, more particularly from variations of oxygen consumption when said muscle is contracted.

More preferably, the increase in muscle mass, muscle strength and/or muscle performance is an increase in muscle mass, muscle strength and/or muscle performance in slow twitch fiber rich muscles of the subject.

The inventors have found that the increase in protein synthesis, and thus the increase in muscle mass, muscle strength and/or muscle performance, correlates with an increase in a specific amino acid in the muscle of the animals: glutamine, which has been shown to play a role in the control of protein synthesis. Thus, the non-therapeutic use of Ncarbamoylputrescine hence directly increases the concentration of this aminoacid in the muscles of the subject, more precisely in slow twitch fiber-rich muscles of the subject.

Preferably, the non-therapeutic use of the invention is to increase the concentration of glutamine in the muscles of the subject.

According to the invention, the term "subject" refers to animals. According to the invention, the term "animal" refers to members of the animal kingdom. Preferably, according to the invention, the term "subject" refers to mammals.

In an embodiment, the subject according to the invention is a human. It is to be understood that, in the context of the non-therapeutic use of the invention, the human subject is a healthy subject, more particularly a subject that does not have a muscle wasting-associated disorder such as herein defined.

Among humans, infants, children in the growing phase, and athletes have in common an elevated muscle protein synthesis: children because of their rapid growth and buildup of muscle tissue, athletes because of further building up muscle mass and performance. Hence it is those persons who will benefit the most from the non-therapeutic administration of N-carbamoylputrescine. In these individuals, the administration of N-carbamoylputrescine will support and possibly enhance physiological protein synthesis rather than prevent or treat a pathological state of the subject.

Preferably, the subject according to the invention is a child, preferably a growing child, or an athlete.

According to the invention, the term "child" refers to a human between the stages of birth and puberty. According to the invention, the terms "growing child" refer to a child whose growth is not yet completed. The growth of a child can be evaluated by the bone development of said child. A child is considered as "grown up" when the carpal and tarsal bones have matured. As a child grows, some parts of the bones become calcified and appear on the x-rays. For example, in a growing child, the carpal and tarsal bones of the hands and feet have not yet completely matured. On the x-rays, they appear separated by a layer of invisible cartilage where most of the growth is occurring. As sex steroid levels rise during puberty, bone maturation accelerates. As growth nears conclusion and attainment of adult height, bones begin to approach the size and shape of adult bones. The remaining cartilaginous portions of the epiphyses become thinner. The child is then considered "grown up" when these cartilaginous zones become obliterated. Until that stage, the child is considered "growing".

According to the invention, the term "athlete" refers to a person possessing the natural or acquired traits, such as strength, agility and endurance that are necessary for physical exercise or sports, especially those performed in competitive contexts. Preferably, in the context of the invention, the term "athlete" refers to a human being practicing intense physical exercise or sports for at least 3 hours a week for at least two consecutive weeks. Metabolic Equivalents (METs) are commonly used to express the intensity of physical activities. MET is the ratio of a person's working metabolic rate relative to their resting metabolic rate. One MET is defined as the energy cost of sitting quietly and is equivalent to a caloric consumption of 1 kcal/kg/hour. By intense physical exercise or sport, it is herein referred to physical exercise of more than 6 METs. It is generally admitted that 6 METs correspond to physical activities inducing a caloric consumption of about 7 kcal/min or more for the subject.

The non-therapeutic use of the invention can also be beneficial for non-human animals, for example for those who are physically active, such as non-human animals taking part in animal racing games and competitions.

In another embodiment, the subject according to the invention is a non-human animal, preferably a non-human mammal. Preferably, the term "non-human animal" includes pigs, cows, poultry, horses, dogs and cats. Even more preferably, the non-human animal according to the invention is a cat, a dog or a pig.

Preferably, in the non-therapeutic use of N-carbamoylputrescine, or one of its salts, an effective amount of said compound is provided to the subject. According to the present invention, an "effective amount" of a compound is one which is sufficient to achieve the desired biological effect. Thus, in the non-therapeutic use according to the invention, an "effective amount" of N-carbamoylputrescine, or one of its salts, is one which is sufficient to enhance muscle protein synthesis in a subject. It is understood that the effective amount will be adapted by the skilled person according to the usual criteria such as for example the age, sex, health of the subject, and the phylum (for example human) of the subject.

Preferably, in the non-therapeutic use according to the invention, N-carbamoylputrescine, or one of its salts, is provided to the human subject at a daily dose of at least 0.01 mg/kg of said subject. More preferably, said daily dose is from 0.1 mg/kg of said subject to 1 mg/kg of said subject.

Preferably, in the non-therapeutic use according to the invention, N-carbamoylputrescine is provided to the non-human subject in a daily dose of at least 0.01 mg/kg of said subject. More preferably, said daily dose is from 0.01 mg/kg of said subject to 10 mg/kg of said subject.

In addition to this first non-therapeutic use, the inventors have surprisingly discovered that N-carbamoylputrescine, or one of its pharmaceutically accepted salts, can advantageously be used as a medicament, and is particularly useful when administered to subjects suffering from a muscle wasting-associated disorder.

Another object of the invention is the use of N-carbamoyl putrescine, or one of its pharmaceutically accepted salts, for its use as a medicament.

Thus, the invention also relates to the use of compound of N-carbamoylputrescine, or one of its pharmaceutically acceptable salts, for the manufacture of a medicament.

By "pharmaceutically acceptable salt", it is herein referred to salts derived from pharmaceutically acceptable inorganic and organic acids. Examples of suitable acids include hydrochloric, sulfuric, nitric, fumaric, maleic, phosphoric, glycolic, lactic, succinic, tartaric, acetic, citric, and methanesulfonic acids.

In an embodiment, said medicament is intended for the prevention and/or treatment of a muscle wasting associated disorder.

Thus, another object of the invention is N-carbamoylputrescine or one of its pharmaceutically accepted salts for use as a medicament in the prevention and/or treatment of a muscle wasting-associated disorder.

In addition, the invention also relates to a method for the prevention and/or treatment of a muscle wasting associated disorder in a human subject in need thereof, comprising administering an effective amount of N-carbamoylputrescine, or one of its pharmaceutically accepted salts, to said subject.

According to the invention, the term "muscle wasting-associated disorder" refers to disorders comprising or caused by muscle atrophy. According to the invention, the terms "muscle wasting" refer to a decrease in the mass and function of said muscle. Muscle wasting has been associated with a large number of disorders, and may for example be present in cachexia, a co-morbidity phenotype which results from several common disorders, such as for example cancers, AIDS, heart failure, COPD (chronic obstructive pulmonary disease), renal failure, sepsis, severe burns and any type of trauma, including post-operative stress. Muscle wasting may also be present in disorders or syndrome associated with aging, such as sarcopenia.

Preferably, the muscle wasting-associated disorder according to the invention is selected from the group consisting of: cachexia, cancer, sepsis, chronic heart failure, rheumatoid arthritis, acquired immune deficiency syndrome, sarcopenia, diabetes, chronic renal failure, burn, and head trauma.

Preferably, in the therapeutic use of N-carbamoylputrescine or one of its pharmaceutically accepted salts, an effective amount of N-carbamoylputrescine or of said salt is provided to the subject.

According to the present invention, an "effective amount" of N-carbamoylputrescine or of one of its pharmaceutically accepted salt is one which is sufficient to achieve the desired biological effect. Thus, in the therapeutic use according to the invention, an "effective amount" of N-carbamoylputrescine or of one of its salt is one which is sufficient for the prevention and/or treatment of muscle wasting in a subject. It is understood that the effective amount will be adapted by the skilled person according to the usual criteria such as for example the age, sex, health of the subject, and the phylum (for example human) of the subject.

Preferably, when N-carbamoylputrescine or one of its salts is used as a medicament intended for the prevention and/or treatment of a muscle wasting-associated disorder, it is to be administered at a daily dose of at least 1 mg/kg of said subject. More preferably, said daily dose is from 1 mg/kg of said subject to 40 mg/kg of said subject, even more preferably from 20 mg/kg of said subject to 40 mg/kg of said subject.

BRIEF DESCRIPTION OF FIGURES

FIG. 1: Effect of administration of NCP on plasma urea, glutamine and ornithine in rats.

Plasma concentrations of urea, glutamine and ornithine were measured in rats untreated (control) (white bars) and rats whose diet consisted of 5 mg/day of NCP (gray bars) for 10 days (thus corresponding to 50 mg/kg of NCP (black bars) The results (mean±SD) are expressed in mmol/l urea and pmol/l amino acids * P<0.05.

EXAMPLES

Reagents

Polyamines and other reagents were from Sigma-Aldrich (L'Isle d'Abeau Chesnes, France).

N-carbamoylputrescine (NCP; Cinoberine™) was synthesized as described in Ramani et al. (Anal. Biochem., 2012, 423(1):54-60)

Animal

Eight-week old Sprague-Dawley rats (Charles Rivers, Lyon, France) were used. They were placed in individual cages and acclimatized for two weeks to our animal facility. During this period they received standard rodent chow (A04, UAR, Villemoisson-sur-Orge, France) and water ad libitum.

Animal care and experimentation complied with French and European Community regulations for animal care and experimentation (Official Journal of the European Community110 L 358, Dec. 18, 1986). The study protocol has been approved by the Regional ethic committee of Ile-de-France.

Animal Experimentation

After acclimatization twenty eight-month old rats were randomized into three groups in order to receive for two weeks a standard diet either alone (n=6; control group) or supplemented with NCP either 5 mg/kg/d (n=7, NCP5 group) or 50 mg/kg/d (n=7; NCP50 group). Their weight, behaviour and mortality were monitored throughout the feeding period.

At the end of the feeding period, the rats, in the fasted state, were anesthetized by isoflurane inhalation and euthanized by decapitation.

Mixed blood was collected onto heparinized tubes and rapidly centrifuged. The liver was immediately removed and weighed, and a sample was cut off, frozen in liquid nitrogen, and stored at −80° C. until analysis. For the jejunum and ileum, the intestine was washed with cold NaCl (0.9%) and reverted. Thereafter the intestinal mucosa was scraped, rapidly frozen in liquid nitrogen, and stored at −80° C. until analysis. Two muscles of the hindlimb, tibialis (rich in type II fibres) and soleus (rich in type I fibres), and the right kidney were rapidly removed, weighed, frozen in liquid nitrogen, and stored at −80° C. until analysis. Body composition was assessed by dissection and lean mass (carcass), visceral fat mass, sub-cutaneous fat mass (subcutaneous fat and skin) and mass of the viscera were determined.

Biological parameters studied were:
  in tissues: NCP, protein and amino acid contents
  in plasma: amino acids, liver function tests (plasma aspartate aminotransferase, alanine aminotransferase, alkaline phosphatase, and bilirubin), muscle enzymes (plasma creatine kinase, and lactate dehydrogenase), plasma electrolytes (sodium, potassium, chloride, bicarbonates), total protein, urea, creatinine, calcium, phosphate, magnesium, uric acid, glucose, cholesterol and triglycerides.

Results

General Effects of N-carbamoyl Putrescine

No rats showed abnormal general behavior, and there was no mortality in the 3 groups during the study.

All animals achieve normal weight gain and there was no difference between rats receiving NCP compared to controls (Table 1).

Analysis of body composition showed no difference between the groups. Lean mass, fat mass, either total, abdominal or cutaneous, mass of the viscera, and liver mass were similar in the three groups (data not shown).

TABLE 1

Influence of NCP on rat weight. Results are presented as mean ± SD

|  | Control (n = 6) | NCP 5 mg/kg (n = 7) | NCP 50 mg/kg (n = 7) |
|---|---|---|---|
| Initial weight (g) | 263.3 ± 11.4 | 264.9 ± 16 | 264.9 ± 8.2 |
| Final weight (g) | 314.2 ± 10.7 | 313.1 ± 18.1 | 316.1 ± 13.9 |
| Weight gain (g) | 50.8 ± 7.9 | 48.1 ± 8.1 | 51.2 ± 8.7 |
| Daily weight gain (g/d) | 3.63 ± 0.57 | 3.44 ± 0.58 | 3.65 ± 0.62 |

Biological Effects of N-carbamoylputrescine

No difference was observed between the three groups in terms of plasma electrolytes levels (sodium, potassium, chloride, bicarbonates, calcium, phosphate, magnesium), in hepatic and muscular enzymes (aminotransferases, creatine kinase, lactate dehydrogenase, alkaline phosphatase), in creatinine, glucose, cholesterol, triglycerides and uric acid levels (data not shown). Plasma urea was higher in NCP50 group vs NCP5 (FIG. 1); however no difference was shown between the two NCP-supplemented groups compared to control rats.

Analysis of amino acid levels showed that plasma glutamine levels were significantly lower in the NCP50 group than in controls (FIG. 1) and there was a trend for a NCP dose-effect relationship (p=0.06). Plasma ornithine showed a similar dose-effect relationship (p=0.055) (FIG. 1). No differences were observed for other amino acids. There was no correlation between plasma urea and plasma glutamine or ornithine.

While liver, kidney, tibialis, and jejunal and ileal mucosa protein contents were similar between the three groups, protein level in soleus was higher in NCP5 vs control group (Control: 12.7±1.8 g/100 g, NCP5: 14.5±0.7 g/100 g, NCP50: 14.0±0.8 g/100 g; p=0.018 NCP5 vs control).

Also, in soleus muscle, while the concentration of most amino acids were similar between the 3 groups, the concentration of Glutamine, alanine and histidine significantly increased with NCP administration and there was a positive correlation for glutamine and alanine with the dose of NCP (p=0.015 and p=0.013 respectively) (Table 2)

TABLE 2

Soleus amino acid content.
Results presented as mean ± SD; ANOVA and plsd Fisher a ≠ b: p ≤ 0

| Amino acid (μmol/g) | Control (n = 6) (1) | NCP 5 mg/kg (n = 7) (2) | NCP 50 mg/kg (n = 6) (3) |
|---|---|---|---|
| Taurine | 22972 ± 3178 | 23882 ± 2585 | 25223 ± 1987 |
| Aspartate | 3889 ± 612 | 4195 ± 703 | 4742 ± 1443 |
| Threonine | 481 ± 75 | 512 ± 109 | 571 ± 67 |
| Serine | 1745 ± 158 | 1933 ± 384 | 1964 ± 248 |
| Asparagine | 447 ± 57 | 519 ± 106 | 538 ± 124 |
| Glutamate | 3757 ± 474 | 3753 ± 684 | 4074 ± 390 |
| Glutamine | 6858 ± 1008$^a$ | 7605 ± 1016$^{ab}$ | 8547 ± 988$^b$ |
| Glycine | 1823 ± 190 | 1932 ± 516 | 2145 ± 153 |
| Alanine | 1539 ± 238$^a$ | 1735 ± 385$^{ab}$ | 2025 ± 182$^b$ |
| Citrulline | 321 ± 33 | 351 ± 53 | 379 ± 65 |
| Valine | 172 ± 38 | 182 ± 22 | 194 ± 24 |
| Isoleucine | 79 ± 25 | 83 ± 17 | 91 ± 22 |
| Leucine | 97 ± 34 | 103 ± 23 | 113 ± 32 |
| Tyrosine | 114 ± 19 | 106 ± 15 | 126 ± 21 |
| Phenylalanine | 77 ± 14 | 75 ± 19 | 77 ± 11 |
| Ornithine | 73 ± 21 | 75 ± 12 | 74 ± 15 |
| Histidine | 406 ± 70$^a$ | 415 ± 50$^a$ | 494 ± 6$^{ab}$ |

TABLE 2-continued

Soleus amino acid content.
Results presented as mean ± SD; ANOVA and plsd Fisher a ≠ b: p < 0

| Amino acid (μmol/g) | Control (n = 6) (1) | NCP 5 mg/kg (n = 7) (2) | NCP 50 mg/kg (n = 6) (3) |
|---|---|---|---|
| Lysine | 877 ± 249 | 933 ± 222 | 1009 ± 168 |
| Arginine | 318 ± 71 | 381 ± 115 | 395 ± 62 |
| Proline | 207 ± 39 | 196 ± 42 | 199 ± 26 |

The invention claimed is:

1. A method of increasing muscle mass or muscle strength comprising administering to a subject in need thereof N-carbamoylputrescine or one of its salts.

2. The method according to claim 1, wherein said method increases glutamine in a muscle of said subject.

3. The method according to claim 1, wherein the subject is a human.

4. The method according to anyone of claim 1, wherein the subject is a non-human animal.

5. A method of treating muscle-wasting associated with a disorder selected from the group consisting of cachexia, cancer, sepsis, chronic heart failure, rheumatoid arthritis, acquired immune deficiency syndrome, sarcopenia, diabetes, chronic renal failure, burn, and head trauma or combinations thereof, comprising administering to a patient in need thereof N-carbamoylputrescine or one of its pharmaceutically accepted salts.

6. The method according to claim 4, wherein the subject is a cat, a dog, or a pig.

7. The method according to claim 1, wherein said subject is at risk of loss of muscle mass, strength or function, or in need of higher muscle mass, strength or function.

8. The method according to claim 3, wherein said subject is a child.

* * * * *